United States Patent
Idage et al.

(10) Patent No.: US 8,895,760 B2
(45) Date of Patent: Nov. 25, 2014

(54) PROCESS FOR THE PREPARATION OF L-LACTIDE OF HIGH CHEMICAL YIELD AND OPTICAL PURITY

(75) Inventors: Bhaskar Bhairavnath Idage, Pune (IN); Susheela Bhaskar Idage, Pune (IN); Sivaram Swaminathan, Pune (IN)

(73) Assignee: Council of Scientific & Industrial Research (IN)

( * ) Notice: Subject to any disclaimer, the term of this patent is extended or adjusted under 35 U.S.C. 154(b) by 116 days.

(21) Appl. No.: 13/595,627

(22) Filed: Aug. 27, 2012

(65) Prior Publication Data
US 2013/0060051 A1    Mar. 7, 2013

Related U.S. Application Data

(63) Continuation of application No. PCT/IN2011/000117, filed on Feb. 25, 2011.

(30) Foreign Application Priority Data

Feb. 26, 2010 (IN) .............................. 435/DEL/2010
Mar. 9, 2010 (IN) .............................. 532/DEL/2010

(51) Int. Cl.
*C07D 319/00* (2006.01)
*C07D 319/12* (2006.01)

(52) U.S. Cl.
CPC ................................... *C07D 319/12* (2013.01)
USPC ....................................................... 549/274

(58) Field of Classification Search
CPC ...................................................... C07D 19/12
USPC ............................................................ 549/274
See application file for complete search history.

(56) References Cited

U.S. PATENT DOCUMENTS

| 3,322,791 | A |   | 5/1967  | Selman            |         |
|-----------|---|---|---------|-------------------|---------|
| 5,023,349 | A |   | 6/1991  | Bhatia            |         |
| 5,053,485 | A |   | 10/1991 | Nieuwenhuis et al.|         |
| 5,053,522 | A |   | 10/1991 | Muller            |         |
| 5,136,057 | A |   | 8/1992  | Bhatia            |         |
| 5,502,215 | A | * | 3/1996  | Yamaguchi et al.  | 549/274 |
| 5,543,494 | A |   | 8/1996  | Perego et al.     |         |

FOREIGN PATENT DOCUMENTS

JP        2000015107 A       1/2000

OTHER PUBLICATIONS

International Search Report; Application No. PCT/IN2011/000117; Issued: Jun. 21, 2011; Mailing Date: Jun. 29, 2011; 6 pages.

\* cited by examiner

*Primary Examiner* — Nizal Chandrakumar
(74) *Attorney, Agent, or Firm* — St. Onge Steward Johnston & Reens LLC

(57) ABSTRACT

A process for the synthesis of 100% optically pure L(+)-lactide catalyzed by zinc and tin metal catalysts of less than 150 micron particle size is disclosed. The L-lactide obtained was further purified to obtain lactide of 100% optical purity and acid impurities less than 10 meq/kg.

11 Claims, No Drawings

PROCESS FOR THE PREPARATION OF L-LACTIDE OF HIGH CHEMICAL YIELD AND OPTICAL PURITY

CROSS-REFERENCE TO RELATED APPLICATIONS

The present application is a continuation of pending International patent application PCT/IN2011/000117 filed on Feb. 25, 2011 which designates the United States and claims priority from Indian patent applications 435/DEL/2010 filed on Feb. 26, 2010, and 532/DEL/2010 filed on Mar. 9, 2010. The content of all prior applications is incorporated herein by reference.

FIELD OF THE INVENTION

The invention relates to an improved process for the preparation of L(+)-lactide of high chemical yield and high optical purity. The invention also relates to a process for the purification of crude lactide to prepare pure L-lactide containing acid impurities less than 10 meq/kg which is polymerized to high molecular weight poly(L-Lactide).

BACKGROUND OF THE INVENTION

Polylactic acid (PLA) is a biodegradable plastic with significantly low potential for causing environmental hazards. Therefore, it has found a wide range of applications including agricultural products, architectural sheets, food wrappings, hygiene materials, fishing nets, fishing lines and various other purposes. It is also widely used for monoaxially and biaxially stretched films, fibers, extrusion products and various other purposes.

Lactic acid has a chiral center and occurs as $_D$-(−) and $_L$-(+) enantiomers. Enantiomeric purity is important for industrial applications and the greatest demand is for the $_L$isomer. Deliberate blending of the enantiomers provides an effective method to control both the physical properties of polylactic acid and the rate of biodegradation. Lactides are dimeric cyclic esters of lactic acid and are the intermediates in the preparation process of high molecular weight polylactides which are truly biodegradable polymers. The optical purity of L(+) lactide is important especially for the preparation of high molecular weight polylactides for the preparation of films and fibers.

Generally, lactic acid is oligomerized and then catalytically dimerized to make the cyclic lactide .monomer. PLA of high molecular weight is produced from the lactide monomer by ring-opening polymerization using most commonly a stannous octoate catalyst or tin (II) chloride. This mechanism does not generate additional water, and hence, a wide range of molecular weights are accessible. Zinc is also a commonly employed catalyst for such reactions. These processes typically lead to PLA in the range of 60-92% with maximum optical purity obtained up to 99.6%.

U.S. Pat. No. 5,053,522 titled, "Process for the preparation of lactide" discloses continuous or semi continuous process for preparing L(−) or D(+)-lactide of substantial optical purity, wherein L(−)-polylactic acid is employed as the starting material to make L(−) lactide and D(+)-polylactic acid is employed as the starting material to make D(+)-lactide. The starting materials used are of 90%-optical purity and wherein the polylactic acid is—heated to about 130° C. to 230° C. under reduced pressure, in the presence of about 0.05 to 1.0 per cent by weight of a catalyst selected from the group consisting of tin dust, tin halide and organic tin compounds derived from C1-C20 carboxylic acids. L-lactide thus obtained has 99% optical purity and yield in the range of 64 to 69%.

JP Publication No. 2000-015107 titled, "Lactidation Catalyst and Preparation of Lactide" by Shimadzu Corp, published on 18.01.2000, discloses a lactic acid oligomer depolymerized by heating under reduced pressure in the presence of a catalyst containing a zinc compound, represented by the formula Zn(OCOR11)(OCOR12) (I) or ZnX1X2 (II) to prepare lactide. The optical purity of the lactide thus obtained is 99.66% and yield is 92%.

U.S. Pat. No. 3,322,791 titled "Preparation of Optically Active Lactides" discloses a process for preparation of substantially pure optically active lactides from optically active lactic acids, wherein, L(+) lactic acid is converted to LH-lactide and D(−)-lactic acid is converted to D(+) lactide, by heating in presence of 0.1-5 weight percent titanium alkoxide.

U.S. Pat. No. 5,023,349 discloses a gas-assisted continuous process for the rapid conversion of oligomers of alpha-hydroxycarboxylic acids, esters or salts thereof to cyclic esters, L-lactide. The oligomer in the reaction zone contains a catalyst (Sn as the metal (powdered)) effective to depolymerize the oligomer to cyclic ester, the catalyst being present in a catalytically effective amount. L-lactide of high purity in high yield is obtained.

However, the said process has its limitations in view of the fact that it is imperative to maintain the flow rate of the gas which should be sufficiently high. If the flow rate is too low, the conversion to cyclic ester is adversely affected leading to lower yields of L-lactide.

Lactide is generally synthesized by the distillation method which uses polylactic acid with a relatively-low molecular weight called "prepolymer" as an intermediate and which comprises the steps of cyclizing this intermediate at a temperature of 180 to 220° C. in the presence of a catalyst thereby forming lactide which is a cyclic ester formed from two molecules of lactic acid and extracting this lactide in the form of vapor out of the reaction system. The lactide vapor expelled by distillation from the reaction part for the synthesis of lactide at any of the steps mentioned above contains lactic acid monomer, lactic acid dimer (lactoyllactic acid), acrylic acid, pyruvic acid and water as impurities. Of these impurities, the acid impurities inconvenience the severance of the polylactic acid chains and the consequent production of high molecular weight polylactic acid by ring opening polymerization.

The impurities are generally removed from crude lactide by methods such as crystallization; extraction or distillation to permit the production of purified lactide. When the separation of lactide from these impurities is effected by crystallization, however, the yield by the crystallization is too low to be commercially acceptable for the production of lactide of high purity. In the separation by distillation, lactic acid and lactide undergo thermal polymerization, hydrolysis and such reactions. Since their thorough separation is difficult and the yield of lactide is low, this method is not acceptable.

The purification of lactide was also performed in a mixture of dual solvent such as acetone and water and claimed to produce lactide of high purity. This method suffers from heavy loss due to the crystallization because the solubility of lactide in acetone is high.

When L-lactic acid is used as the raw material for the crude lactide, the lactic acid undergoes racemization and gives rise to meso-lactide and a minute amount of D-lactide in addition to L-lactide, because high reaction temperature and long retention time must be used generally for allowing the reaction to proceed.

U.S. Pat. No. 5,502,215 titled "Method for purification of lactide" discloses washing of crude (L/D) lactide with cold water at 20° C. to remove/control the water soluble impurities such as meso-lactide and lactic acid monomer. Further, the lactide crystals are recrystallised from boiling acetone.

U.S. Pat. No. 5,053,485 titled "Polymer lactide, method for preparing it and a composition containing it" describe the purification of crude DL-lactide by using inexpensive solvents, such as toluene, benzene and diethyl ether.

U.S. Pat. No. 5,136,057 claims a process for preparing lactide by depolymerization of a polylactide. The depolymerised product is scrubbed with a solvent such as acetone, to form a solution of lactide and its lactic acid value impurities. The solution is further concentrated to start precipitation of lactide, and diluted with water, preferably water cooled to 0°-5° C., in an amount sufficient to precipitate the lactide substantially, leaving the lactic acid values in the aqueous acetone solution. Lactide, substantially free of its impurities, is separated, and purified further, by-washing, drying and recrystallization from non-reactive solvents, e.g., toluene. 50% yield in cycle 1 with yields increasing to 70 and 84% in cycles 2 and 3.

U.S. Pat. No. 5,543,494 titled "Process for the production of poly (lactic acid)" discloses purification of L-lactide by boiling with anhydrous toluene and also successive washings with anhydrous cold toluene is disclosed yielding 60% of L-lactide.

Further, for the purpose of synthesizing polylactic acid with a high molecular weight and having a high optical purity, it is necessary that the lactic acids which are components of the lactide being used as the raw material posses a high optical purity, namely the lactide itself should possess a high optical purity.

Thus there is no process in the art for the preparation of L-lactide which could give the product in high yield and having an optical purity of 100%. Further, it is observed that yield and optical purity of L-lactide is sensitive to temperature, pressure, catalyst used etc. Also, preparation by batch wise-operating process leads to deterioration in the overall-yield and to a reduction in optical purity.

SUMMARY OF THE INVENTION

The main objective of the present invention to provide an improved process for the preparation of 100% optically pure lactide, in particular optically pure L(+)-lactide.

A further objective of the present invention to provide an improved process for the preparation of 100% optically pure lactide with 99% yield.

A further objective of the present invention is to develop an improved process that is simple, employs commonly available catalysts to obtain optically pure lactide in high yields.

A further objective of the present invention is to develop a method for the purification of lactide with a view to prepare optically pure L(+)-lactide which can be further polymerized to high molecular weight poly(L-lactide) by ring opening polymerization.

Another objective of the invention is to provide a process for the synthesis of optically pure L(+)-lactide with acid impurities less than 10 meq/kg.

Accordingly, the present invention provides an improved process for the preparation of L(+)-lactide of high chemical yield and high optical purity. The invention also relates to a process for the purification of crude lactide to prepare pure L-lactide containing acid impurities less than 10 meq/kg which is polymerized to high molecular weight poly(L-Lactide).

In an attempt to obtain 100% L(+) lactide in good yield the inventors observed that decreasing the particle size of the catalysts resulted in higher yields of the product. Thus, the invention provides an improved process for the synthesis of 100% optically pure L(+) lactide catalyzed by zinc or tin metal catalysts. The lactide obtained by present purification process contains acid impurities less than 10 meq/kg, preferably less than 5 meq/kg, more preferably less than 1 meq/kg and optical purity of 100%.

In an embodiment of the present invention, an improved process for the preparation of 100% optically pure L(+) lactide catalyzed by metal catalyst, wherein said process comprising the steps of;

a. charging L(+)-lactic acid in a reactor, subjecting it to melt polymerization consecutively at temperature ranging 150° C. to 160° C. for a period ranging between 2 to 3 h under nitrogen atmosphere followed at temperature ranges between 150 to 160° C. for 1.5 to 2 h at 100-110 mm. Hg further followed at 150-160° C. for 1.5 to 2 h at 30-40 mm. Hg and finally carried out melt polymerization at 150 to 160° C. for 1 to 1.5 h at 0.01 to 0.1 mm. Hg with continuous stirring at 60-70 RPM to obtain viscous oligomer;

b. cooling the viscous oligomer material as obtained in step (a) to room temperature ranging between 25-30° C. under nitrogen flow;

c. charging oligomer obtained in step (b) and a metal catalyst ranging between 0.1 to 0.5 wt % based on oligomer in a reactor;

d. depolymerizing of oligomers as obtained in step (c) consecutively at 160 to 170° C. for 1 to 1.5 h under nitrogen atmosphere followed at temperature ranging between 170 to 180° C. for 1 to 1.5 h at 100-110 mm. Hg, further followed at 180 to 190° C. for 1 to 1.5 h at 10 to 20 mm. Hg and finally carried out depolymerization at 190 to 200° C. for 2 to 2.5 h at 0.01 to 0.1 mm. Hg to obtain the crude lactide;

e. purifying the crude lactide as obtained in step (d) from a solvent to obtain pure lactide.

In another embodiment of the invention, metal catalysts used in step (c) are selected from Tin or Zinc.

In another embodiment of the invention, wherein solvent used in step (e) is ethyl acetate.

In another embodiment of the invention, wherein particle size of catalyst is less than 150 microns.

In another embodiment of the invention, wherein yield of optical pure L(+)-lactide is up to 99%.

In another embodiment of the invention, A process for the purification of crude lactide to obtain pure (L) lactide with 100% optical purity containing acid impurities less than 10 meq/kg, preferably less than 5 meq/kg comprising the following steps:

a. crystallizing crude lactide from boiling anhydrous toluene;

b. Separating toluene crystallized lactide by filtration;

c. Washing of lactide crystals with cold toluene;

d. Washing of lactide crystals with water at less than 10° C., preferably 0-5° C.; and e. Drying said lactide crystals under reduced pressure.

In another embodiment of the invention, wherein, washing of the lactide crystals optionally washed with anhydrous ethylacetate prior to drying.

DETAILED DESCRIPTION OF THE INVENTION

In the invention L(+)-lactic acid is oligomerized to obtain a yield of about 98%. The oligomer is then reacted with 0.5% by its weight of the metal catalyst selected from tin (example 1) of particle size greater than 150 μm to obtain 70% yield of lactide based on the weight of oligomer. The resultant L(+)-lactide formed is 97% optically pure. However, when the polymerization is carried out with tin catalyst of less than 150 μm (examples 2 to 6 respectively) or zinc catalyst of less than 10 μm particle size (example 8) yielded 100% optically pure L(+)-lactide. The yield of the reaction is 98%.

The following examples are given to illustrate the process of the present invention and should not be construed to limit the scope of the present invention.

Example 1

Preparation of Polylactic Acid Oligomer

A 1 L three-necked cylindrical glass reactor equipped with a mechanical stirrer, a nitrogen gas inlet and a vacuum jacketed Vigreux column and distillation head was charged with 700 g of L(+)-lactic acid (90%). The melt polymerization was carried out at 150° C. for 2 h under nitrogen atmosphere; 150° C. for 1.5 h at 100 mm Hg; 150° C. for 1.5 h at 30 mm Hg and finally at 150° C. for 1 h at 0.01 mm Hg. The stirring speed was maintained at 70 RPM throughout the melt polymerization. The viscous material obtained was cooled at 25° C. under the flow of nitrogen and characterized by vapour pressure osmometer (VPO). Yield: 493 g (98%), $M_n$=1100 g/mol.

Preparation of Lactide

A 1 L three-necked cylindrical glass reactor was equipped with a mechanical stirrer, a distillation condenser and a coiled receiver trap. The reactor was charged with 493 g of polylactic acid oligomer (number average molecular weight 1100) and 2.46 g (0.5 wt % based on oligomer) of tin powder (>150 μm) as a catalyst. The depolymerization was carried out at 160° C. for 1 h under nitrogen atmosphere; 180° C. for 1 h at 100 mm. Hg; 190° C. for 1 h at 10 mm. Hg and finally at 200° C. for 2 h at 0.01 mm. Hg. The depolymerization of polylactic acid oligomer is a slow process. Therefore, the depolymerization is carried out under reduced pressure at different temp/time profiles and the lactide formed is continuously collected in the receiver container.

At the end of the above reaction period, 345 g (70% based on polylactic acid oligomer) of lactide was obtained. The lactide was further purified by crystallization from ethyl acetate and characterized by HPLC using chiral columns. The chiral purity of purified lactide was 95% of L(+)-lactide. Yield: 70%

Example 2

Polylactic acid oligomer was prepared from L(+)-lactic acid by following the experimental procedure given in Example 1.

Preparation of Lactide

A 1 L three-necked cylindrical glass reactor was equipped with a mechanical stirrer, a distillation condenser and a coiled receiver trap. The reactor was charged with 493 g of polylactic acid oligomer (number average molecular weight 1100) and 0.492 g (0.1 wt % based on oligomer) of tin powder (<150 μm) as a catalyst. The depolymerization was carried out at 160° C. for 1 h under nitrogen atmosphere; 180° C. for 1 h at 100 mm. Hg; 190° C. for 1 h at 10 mm. Hg and finally at 200° C. for 2 h at 0.01 mm. Hg. At the end of the above reaction period, 433 g (88% based on polylactic acid oligomer) of lactide was obtained. The lactide was further purified and characterized by HPLC using chiral columns. The chiral purity of purified lactide was 100% of L(+)-lactide. Yield: 88%

Example 3

Polylactic acid oligomer was prepared from L(+)-lactic acid by following the experimental procedure given in Example 1.

Preparation of Lactide

A 1 L three-necked cylindrical glass reactor was equipped with a mechanical stirrer, a distillation condenser and a coiled receiver trap. The reactor was charged with 493 g of polylactic acid oligomer (number average molecular weight 1100) and 0.984 g (0.2 wt % based on oligomer) of tin powder (<150 μm) as a catalyst. The depolymerization was carried out at 160° C. for 1 h under nitrogen atmosphere; 180° C. for 1 h at 100 mm. Hg; 190° C. for 1 h at 10 mm. Hg and finally at 200° C. for 2 h at 0.01 mm. Hg. At the end of the above reaction period, 443 g (90% based on polylactic acid oligomer) of lactide was obtained. The lactide was further purified and characterized by HPLC using chiral columns. The chiral purity of purified lactide was 100% of L(+) lactide. Yield: 90%

Example 4

Polylactic acid oligomer was prepared from L(+)-Lactic acid by following the experimental procedure given in Example 1.

Preparation of Lactide

A 1 L three-necked cylindrical glass reactor was equipped with a mechanical stirrer, a distillation condenser and a coiled receiver trap. The reactor was charged with 493 g of polylactic acid oligomer (number average molecular weight 1100) and 1.476 g (0.3 wt % based on oligomer) of tin powder (<150 μm) as a catalyst. The depolymerization was carried out at 160° C. for 1 h under nitrogen atmosphere; 180° C. for 1 h at 100 mm. Hg; 190° C. for 1 h at 10 mm. Hg and finally at 200° C. for 2 h at 0.01 mm. Hg. At the end of the above reaction period, 458 g (93% based on polylactic acid oligomer) of lactide was obtained. The lactide was further purified and characterized by HPLC using chiral columns. The chiral purity of purified lactide was 100% of L(+) lactide. Yield: 93%

Example 5

Polylactic acid oligomer was prepared from L(+)-lactic acid by following the experimental procedure given in Example 1.

Preparation of Lactide

A 1 L three-necked cylindrical glass reactor was equipped with a mechanical stirrer, a distillation condenser and a coiled receiver trap. The reactor was charged with 493 g of polylactic acid oligomer (number average molecular weight 1100) and 1.968 g (0.4 wt % based on oligomer) of tin powder (<150 μm) as a catalyst. The depolymerization was carried out at 160° C. for 1 h under nitrogen atmosphere: 180° C. for 1 h at 100 mm. Hg: 190° C. for 1 h at 10 mm. Hg and finally at 200° C. for 2 h at 0.01 mm. Hg. At the end of the above reaction period, 473 g (96% based on polylactic acid oligomer) of lactide was obtained. The lactide was further purified and characterized by HPLC using chiral columns. The chiral purity of purified lactide was 100% of L(+)-lactide. Yield: 96%

Example 6

Polylactic acid oligomer was prepared from L(+)-lactic acid by following the experimental procedure given in Example 1.

Preparation of Lactide

A 1 L three-necked cylindrical glass reactor was equipped with a mechanical stirrer, a distillation condenser and a coiled receiver trap. The reactor was charged with 493 g of polylactic acid oligomer (number average molecular weight 1100) and 2.46 g (0.5 wt % based on oligomer) of tin powder (<150 μm) as a catalyst. The depolymerization was carried out at 160° C. for 1 h under nitrogen atmosphere; 180° C. for 1 h at 100 mm. Hg; 190° C. for 1 h at 10 mm. Hg and finally at 200° C. for 2 h at 0.01 mm. Hg. At the end of the above reaction period, 488 g (99% based on polylactic acid oligomer) of lactide was obtained. The lactide was further purified and characterized by HPLC using chiral columns. The chiral purity of purified lactide was 100% of L(+)-lactide. Yield: 99%

The use of dry tin powder (<150 μm) catalyst accelerates the rate of depolymerization of polylactic acid oligomer. The yield of lactide increases with increase in the concentration of tin powder. Furthermore, the yield of lactide in Example 6 is higher as compared to Example 2.

TABLE 1

Preparation of lactide
Catalyst: Tin powder
Particle size: <150 μm

| Example | Tin powder (wt %) | Lactide Yield | Optical Purity (L+) (%) |
|---|---|---|---|
| 1* | 0.5 | 70 | 95 |
| 2 | 0.1 | 88 | 100 |
| 3 | 0.2 | 90 | 100 |
| 4 | 0.3 | 93 | 100 |
| 5 | 0.4 | 96 | 100 |
| 6 | 0.5 | 99 | 100 |

*Particle size: >150 μm

Example 7

Polylactic acid oligomer was prepared from L (+)-Lactic acid by following the experimental procedure given in Example 1.

Preparation of Lactide

A 1 L three-necked cylindrical glass reactor was equipped with a mechanical stirrer, a distillation condenser and a coiled receiver trap. The reactor was charged with 493 g of polylactic acid oligomer (number average molecular weight 1100) and 2.46 g (0.5. wt % based on oligomer) of zinc dust (>150 μm) as a catalyst. The depolymerization was carried out at 160° C. for 1 h under nitrogen atmosphere; 180° C. for 1 h at 100 mm. Hg; 190° C. for 1 h at 10 mm. Hg and finally at 200° C. for 2 h at 0.01 mm. Hg. At the end of the above reaction period, 345 g (70% based on polylactic acid oligomer) of lactide was obtained. The lactide was further purified and characterized by HPLC using chiral columns. The chiral purity of purified lactide was 97% of L(+) lactide. Yield: 70%

Example 8

Polylactic acid oligomer was prepared from L(+)-lactic acid by following the experimental procedure given in Example 1.

Preparation of Lactide

A 1 L three-necked cylindrical glass reactor was equipped with a mechanical stirrer, a distillation condenser and a coiled receiver trap. The reactor was charged with 493 g of polylactic acid oligomer (number average molecular weight 1100) and 2.46 g (0.5 wt % based on oligomer) of zinc powder (<10 μm) as a catalyst. The depolymerization was carried out at 160° C. for 1 h under nitrogen atmosphere; 180° C. for 1 h at 100 mm. Hg; 190° C. for 1 h at 10 mm. Hg and finally at 200° C. for 2 h at 0.01 mm. Hg. At the end of the above reaction period, 483 g (98% based on polylactic acid oligomer) of lactide was obtained. The lactide was further purified and characterized HPLC using chiral columns. The chiral purity of purified lactide was 100% of L(+) lactide. Yield: 98%

The use of dry zinc powder (<10 μm) catalyst accelerates the rate of depolymerization of polylactic acid oligomer. The yield of lactide is also higher as compared to Example 7.

Example 9

Preparation of L-Lactide

A 1 L three-necked cylindrical glass reactor was equipped with a mechanical stirrer, a distillation condenser and a coiled receiver trap. The reactor was charged with 493 g of polylactic acid oligomer (number average molecular weight 1100) and 2.46 g (0.5 wt % based on oligomer) of tin powder (<10 micron) as a catalyst. The depolymerization was carried out at 160° C. for 1 h under nitrogen atmosphere; 180° C. for 1 h at 100 mm. Hg; 190° C. for 1 h at 10 mm. Hg and finally at 200° C. for 2 h at 0.01 mm. Hg. At the end of the above reaction period, 488 g (99% based on polylactic acid oligomer) of lactide was obtained. The crude lactide obtained was analyzed for the optical purity and free acid content. The optical purity (L+) was found to be 99% and the free acid content was found to be 360 meq/kg of lactide.

Preparation of Poly(L-Lactic Acid)

A 50 mL glass ampoule was charged with 10 g of crude lactide (Free acid content: 360 meq/kg) with the aid of a small funnel under dry nitrogen atmosphere. To it was added 0.5 ml of a 1% by weight solution of tin octoate in toluene under dry nitrogen. The content in the glass ampoule was dried at 60-70° C. under reduced pressure (0.01 mbar) for 1 h. The glass ampoule was then sealed with gas burner and the polymerization is carried out at 200° C. for 1 h. The glass clear polymer obtained was separated from the glass ampoule and characterized by gel permeation chromatography (GPC). The polylactic acid had Mn=11,300 g/mol, Mw=18,200 g/mol, Mw/Mn=1.61.

Example 10

Purification of L-Lactide

To a 2 Liter round bottom equipped with magnetic stirring were added 488 g of the crude L-lactide produced in the Example 9 and 500 mL of distilled water (10° C.). The mixture was stirred for 0.5 h and lactide was separated by filtration under nitrogen and dried at 60° C. for 4 h under reduced pressure. 365 g of L-lactide which was equal to a yield of 75% was obtained with a melting point of 97° C. The crude lactide obtained was analyzed for the optical purity and free acid content. The optical purity (L+) was found to be 100% and the free acid content was found to be <240 meq/kg of lactide.

Preparation of Poly(L-Lactic Acid)

A 50 mL glass ampoule was charged with 10 g of purified L-lactide (Free acid content: 240 meq/kg) with the aid of a small funnel under dry nitrogen atmosphere. To it was added 0.5 ml of a 1% by weight solution of tin octoate in toluene under dry nitrogen. The content in the glass ampoule was dried at 60-70° C. under reduced pressure (0.01 mbar) for 1 h. The glass ampoule was then sealed with gas burner and the polymerization is carried out at 200° C. for 1 h. The glass clear polymer obtained was separated from the glass ampoule and characterized by gel permeation chromatography (GPC). The polylactic acid had Mn=15,300 g/mol, Mw=24,700 g/mol, Mw/Mn=1.62.

Example 11

Purification of L-Lactide

To a 2 Liter round bottom flask equipped with Dean Stark apparatus, magnetic stirring and reflux condenser were added 488 g of the crude L-lactide produced in the Example 9 and 500 mL of anhydrous toluene. The mixture was brought to boiling point and refluxed till the complete evolution of water present in the lactide. The water collected in the Dean Stark apparatus was removed and the solution was allowed to crystallize the L-lactide. The L-lactide thus crystallized was filtered under nitrogen, washed with two portions of anhydrous and cold toluene and dried at 60° C. for 4 h under reduced pressure. 449 g of L-lactide which was equal to a yield of 92% was obtained with a melting point of 97° C. The toluene crystallized lactide was analyzed for the optical purity and free acid content. The optical purity (L+) was found to be 99% and the free acid content was found to be 160 meq/kg of lactide.

Preparation of Poly(L-Lactic Acid)

A 50 mL glass ampoule was charged with 10 g of toluene crystallized L-lactide (Free acid content: 160 meq/kg) with the aid of a small funnel under dry nitrogen atmosphere. To it was added 0.5 ml of a 1% by weight solution of tin octoate in toluene under dry nitrogen. The content in the glass ampoule was dried at 60-70° C. under reduced pressure (0.01 mbar) for 1 h. The glass ampoule was then sealed with gas burner and the polymerization is carried out at 200° C. for 1 h. The glass clear polymer obtained was separated from the glass ampoule and characterized by gel permeation chromatography (GPC). The polylactic acid had Mn=21,700 g/mol, Mw=35,200 g/mol, Mw/Mn=1.62

Example 12

Purification of L-Lactide

To a 2 Liter round bottom flask equipped with Dean Stark apparatus, magnetic stirring and reflux condenser were added 488 g of the crude L-lactide produced in the Example 9 and 500 mL of anhydrous toluene. The mixture was brought to boiling point and refluxed till the complete evolution of water present in the lactide. The water collected in the Dean Stark apparatus was removed and the solution was allowed to crystallize the L-lactide. The L-lactide thus crystallized was filtered under nitrogen, washed with anhydrous and cold toluene. The crystallized lactide was again washed two times with distilled water (0° C.) and dried at 70° C. for 4 h under reduced pressure. 439 g of L-lactide which was equal to a yield of 90% was obtained with a melting point of 97° C. The crude lactide obtained was analyzed for the optical purity and free acid content. The optical purity (L+) was found to be 100% and the free acid content was found to be 9 meq/kg of lactide.

Preparation of Poly(L-Lactic Acid)

A 50 mL glass ampoule was charged with 10 g of purified L-lactide (Free acid content: 9 meq/kg) with the aid of a small funnel under dry nitrogen atmosphere. To it was added 0.5 ml of a 1% by weight solution of tin octoate in toluene under dry nitrogen. The content in the glass ampoule was dried at 60-70° C. under reduced pressure (0.01 mbar) for 1 h. The glass ampoule was then sealed with gas burner and the polymerization is carried out at 200° C. for 1 h. The glass clear polymer obtained was separated from the glass ampoule and characterized by gel permeation chromatography (GPC). The polylactic acid had Mn=99,300 g/mol, Mw=1,66,400 g/mol, Mw/Mn=1.67.

Example 13

Purification of L-Lactide

To a 2 Liter round bottom flask equipped with Dean Stark apparatus, magnetic stirring and reflux condenser were added 488 g of the crude L-lactide produced in the Example 9 and 500 mL of anhydrous toluene. The mixture was brought to boiling point and refluxed till the complete evolution of water present in the lactide. The water collected in the Dean Stark apparatus was removed and the solution was allowed to crystallize the L-lactide. The L-lactide thus crystallized was filtered under nitrogen, washed with anhydrous and cold toluene. The crystallized lactide was again washed two times with distilled water (10° C.) and dried at 70° C. for 4 h under reduced pressure. 400 g of L-lactide which was equal to a yield of 82% was obtained with a melting point of 97° C. The crude lactide obtained was analyzed for the optical purity and free acid content. The optical purity (L+) was found to be 100% and the free acid content was found to be 8 meq/kg of lactide.

Preparation of Poly(L-Lactic Acid)

A 50 mL glass ampoule was charged with 10 g of purified L-lactide (Free acid content: 8 meq/kg) with the aid of a small funnel under dry nitrogen atmosphere. To it was added 0.5 ml of a 1% by weight solution of tin octoate in toluene under dry nitrogen. The content in the glass ampoule was dried at 60-70° C. under reduced pressure (0.01 mbar) for 1 h. The glass ampoule was then sealed with gas burner and the polymerization is carried out at 200° C. for 1 h. The glass clear polymer obtained was separated from the glass ampoule and characterized by gel permeation chromatography (GPC). The polylactic acid had Mn=75,400 g/mol, Mw=1,24,300 g/mol, Mw/Mn=1.64

Example 14

Purification of L-Lactide

To a 2 Liter round bottom flask equipped with Dean Stark apparatus, magnetic stirring and reflux condenser were added 488 g of the crude L-lactide produced in the Example 9 and 500 mL of anhydrous toluene. The mixture was brought to boiling point and refluxed till the complete evolution of water present in the lactide. The water collected in the Dean Stark apparatus was removed and the solution was allowed to crystallize the L-lactide. The L-lactide thus crystallized was filtered under nitrogen, washed with, anhydrous and cold toluene. The crystallized lactide was again washed two times with distilled water (20° C.) and dried at 70° C. for 4 h under reduced pressure. 342 g of L-lactide which was equal to a yield of 70% was obtained with a melting point of 97° C. The crude lactide obtained was analyzed for the optical purity and free acid content. The optical purity (L+) was found to be 100% and the free acid content was found to be 6 meq/kg of lactide.

Preparation of Poly(L-Lactic Acid)

A 50 mL glass ampoule was charged with 10 g of purified L-lactide (Free acid content: 6 meq/kg) with the aid of a small funnel under dry nitrogen atmosphere. To it was added 0.5 ml of a 1% by weight solution of tin octoate in toluene under dry nitrogen. The content in the glass ampoule was dried at 60-70° C. under reduced pressure (0.01 mbar) for 1 h. The glass ampoule was then sealed with gas burner and the polymerization is carried out at 200° C. for 1 h. The glass clear polymer obtained was separated from the glass ampoule and characterized by gel permeation chromatography (GPC). The polylactic acid had Mn=82,700 g/mol, Mw=1,34,000 g/mol, Mw/Mn=1.62

Example 15

Purification of L-Lactide

To a 2 Liter round bottom flask equipped with Dean Stark apparatus, magnetic stirring and reflux condenser were added 488 g of the crude L-lactide produced in the Example 9 and 500 mL of anhydrous toluene. The mixture was brought to boiling point and refluxed till the complete evolution of water present in the lactide. The water collected in the Dean Stark apparatus was removed and the solution was allowed to crystallize the L-lactide. The L-lactide thus crystallized was filtered under nitrogen, washed with anhydrous and cold toluene. The crystallized lactide was again washed two times with distilled water (30° C.) and dried at 70° C. for 4 h under reduced pressure. 244 g of L-lactide which was equal to a yield of 50% was obtained with a melting point of 97° C. The crude lactide obtained was analyzed for the optical purity and free acid content. The optical purity (L+) was found to be 100% and the free acid content was found to be 4 meq/kg of lactide.

Preparation of Poly(L-Lactic Acid)

A 50 mL glass ampoule was charged with 10 g of purified L-lactide (Free acid content: 4 meq/kg) with the aid of a small funnel under dry nitrogen atmosphere. To it was added 0.5 ml of a 1% by weight solution of tin octoate in toluene under dry nitrogen. The content in the glass ampoule was dried at 60-70° C. under reduced pressure (0.01 mbar) for 1 h. The glass ampoule was then sealed with gas burner and the polymerization is carried out at 200° C. for 1 h. The glass clear polymer obtained was separated from the glass ampoule and characterized by gel permeation chromatography (GPC). The polylactic acid had Mn=95,800 g/mol, Mw=1,57,000 g/mol, Mw/Mn=1.63.

Example 16

Purification of L-Lactide

To a 2 Liter round bottom flask equipped with Dean Stark apparatus, magnetic stirring and reflux condenser were added 488 g of the crude L-lactide produced in the Example 9 and 500 mL of anhydrous toluene. The mixture was brought to boiling point and refluxed till the complete evolution of water present in the lactide. The water collected in the Dean Stark apparatus was removed and the solution was allowed to crystallize the L-lactide. The L-lactide thus crystallized was filtered under nitrogen, washed with anhydrous and cold toluene. The crystallized lactide was again washed two times with distilled water (0° C.), dried at 60° C. under reduced pressure, recrystallized from dry ethyl acetate and again dried at 60° C. for 4 h under reduced pressure. 342 g of L-lactide which was equal to a yield of 70% was obtained with a melting point of 97° C. The crude lactide obtained was analyzed for the optical purity and free acid content. The optical purity (L+) was found to be 100% and the free acid content was found to be <1 meq/kg of lactide.

Preparation of Poly(L-Lactic Acid)

A 50 mL glass ampoule was charged with 10 g of purified L-lactide (Free acid content: <1 meq/kg) with the aid of a small funnel under dry nitrogen atmosphere. To it was added 0.5 ml of a 1% by weight solution of tin octoate in toluene under dry nitrogen. The content in the glass ampoule was dried at 60-70° C. under reduced pressure (0.01 mbar) for 1 h. The glass ampoule was then sealed with gas burner and the polymerization is carried out at 200° C. for 1 h. The glass clear polymer obtained was separated from the glass ampoule and characterized by gel permeation chromatography (GPC).

The polylactic acid had Mn=1,36,000 g/mol, Mw=2,24,000 g/mol, Mw/Mn=1.64.

Advantages

The use of metal catalyst namely tin (<150 μm) and zinc (<10 μm) gives L-Lactide of high chemical yield (>98%) and optical purity (L+: 100%) on depolymerization of polylactic acid oligomer at different temperature/time profiles which is required for the manufacture of films and fibers.

Another advantage of present invention for the purification of lactide with a view to prepare optically pure L(+) lactide which can be further polymerized to high molecular weight poly(L-lactide) by ring opening polymerization.

What is claimed is:

1. A process for the preparation of 100% optically pure L(+)-lactide, said process comprising the steps of:
  a. charging L(+)-lactic acid in a reactor, subjecting it to melt polymerization in consecutive steps, initially at 150° C. to 160° C. for 2 hours to 3 hours under a nitrogen atmosphere, then at a temperature of 150° C. to 160° C. for 1.5 hours to 2 hours at 100-110 mm Hg, then at 50° C. to 160° C. for 1.5 hours to 2 hours at 30-40 mm Hg, and finally at 150° C. to 160° C. for 1 hour to 1.5 hours at 0.01 to 0.1 mm Hg with continuous stirring at 60-70 RPM to obtain a viscous oligomer;
  b. cooling the viscous oligomer obtained in step (a) to a temperature of between 25° C. to 30° C. under nitrogen flow;
  c. adding a tin metal catalyst having a particle size of less than 150 microns or a zinc metal catalyst having a particle size of less than 10 microns to the viscous oligomer obtained in step (b), in an amount which is 0.1 wt % to 0.5 wt % of the weight of the viscous oligomer in the reactor to form a mixture;
  d. deploymerizing the mixture of step (c) in consecutive steps, initially at 160° C. to 170° C. for 1 hour to 1.5 hours under nitrogen atmosphere, then at 170° C. to 180° C. for 1 hour to 1.5 hours at 100-110 mm Hg, then at 180° C. to 190° C. for 1 hour to 1.5 hours at 10 to 20 mm Hg, and finally at 190° C. to 200° C. for 2 hours to 2.5 hours at 0.01 to 0.1 mm Hg to obtain a crude lactide;
  e. purifying the crude lactide obtained in step (d) by crystallization from a solvent to obtain pure L(+) lactide.

2. The process as claimed in claim 1, wherein the solvent used in step (e) is ethyl acetate.

3. The process as claimed in claim 1, wherein the tin metal catalyst is used in step (c).

4. The process as claimed in claim 1, wherein the yield of pure L(+) lactide is up to 99%.

5. The process as claimed in claim 1, wherein the step of purifying the crude lactide to obtain pure (L)-lactide, comprises the following steps:
  a. crystallizing crude lactide in boiling anhydrous toluene;
  b. separating toluene from crystallized lactide by filtration;
  c. washing of lactide crystals with cold toluene;
  d. washing of lactide crystals with water at less than 10° C.; and
  e. drying said lactide crystals under reduced pressure; said lactide crystals having 100% optical purity and less than 10 meq/kg of acid impurities.

6. The process as claimed in claim 5, wherein, said lactide crystals are washed with anhydrous ethyl acetate prior to drying.

7. The process as claimed in claim 5, said lactide crystals having less than 5 meq/kg of acid impurities.

8. The process as claimed in claim 5, wherein the water used in said step of washing of lactide crystals with water is at 0-5° C.

9. The process as claimed in claim 1, wherein the zinc metal catalyst is used in step (c).

10. The process of claim 5, further comprising:
   adding a solution of tin octoate in toluene to the lactide crystals under dry nitrogen, followed by drying the resulting mixture at 60° C. to 70° C. under a reduced pressure for 1 hour to form a dried mixture;
   polymerizing the lactide crystals in the dried mixture at 200° C. for 1 hour to yield a high molecular weight poly(L-lactic acid).

11. The process of claim 10, wherein the Mw of said poly(L-lactic acid) is in the range of 124,300 to 224,000.

\* \* \* \* \*